United States Patent [19]

Ueno

[11] Patent Number: 5,162,370

[45] Date of Patent: Nov. 10, 1992

[54] TREATMENT OF CATARACT WITH PROSTACYCLIN COMPOUNDS

[75] Inventor: Ryuji Ueno, Hyogo, Japan

[73] Assignee: K. K. Ueno Seiyaku Oyo Kenkyujo, Osaka, Japan

[21] Appl. No.: 739,069

[22] Filed: Aug. 1, 1991

[30] Foreign Application Priority Data

Aug. 2, 1990 [JP] Japan .................................. 2-206450

[51] Int. Cl.$^5$ ..................... A61K 31/21; A61K 31/40; A61K 31/12; A61K 31/045
[52] U.S. Cl. ..................................... 514/510; 514/63; 514/412; 514/421; 514/443; 514/469; 514/470; 514/690; 514/729
[58] Field of Search ............... 514/573, 530, 912, 469, 514/470, 443, 421, 412, 510, 690, 729, 63

[56] References Cited

FOREIGN PATENT DOCUMENTS 0134153 8/1984 European Pat. Off. .
2017699 3/1979 United Kingdom .

*Primary Examiner*—Frederick E. Waddell
*Assistant Examiner*—Zohreh A. Fay
*Attorney, Agent, or Firm*—Sughrue, Mion, Zinn, Macpeak & Seas

[57] ABSTRACT

A method for treatment of cataract which comprises administering, to a subject in need of such treatment, a prostacyclin compound in an amount effective in treatment of cataract.

4 Claims, No Drawings

TREATMENT OF CATARACT WITH PROSTACYCLIN COMPOUNDS

BACKGROUND OF THE INVENTION

1. Field of the Invention

The present invention relates to a method for treatment of cataract which comprises administering a prostacyclin compound to a subject.

Prostacyclin is (called) another name of prostaglandin $I_2$.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

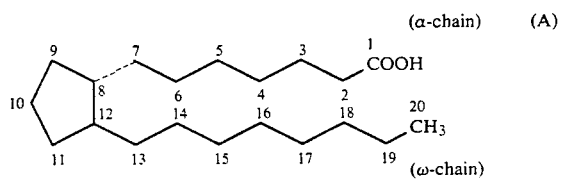

The PGs are classified based on the structural feature of five-membered ring moiety into PGAs, PGBs, PGCs, PGDs, PGEs, PGFs, PGGs, PGHs and PGJs, while PGIs have an different skeleton, shown below, formed by cyclization between the α-chain and the five-membered ring.

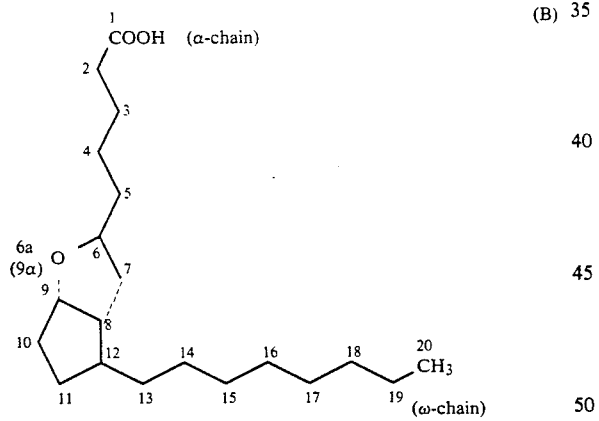

Some of synthetic analogues have somewhat modified skeletons. These are further classified based on the presence or absence of unsaturation and oxidation in the chain moiety as:

Subscript 1—13,14-unsaturated-15-OH
Subscript 2—5,6- and 13,14-diunsaturated-15-OH
Subscript 3—5,6- 13,14- and 17,18- triunsaturated-15-OH

2. Background Information

Natural $PGI_2$ is known to have an action of inhibiting platelet aggregation and hypotensive activity. Further, carbacyclin (also known as 9(0)-methanoprostacyclin or 9(O)-methano-$PGI_2$), which is a synthetic PG derivative having a methylene group in place of the oxygen at position 6a(9α) of $PGI_2$, is known to have an action of inhibiting platelet aggregation. Also, compound having a nitrogen in place of the oxygen at position 6a(9α) and a sulfur in place of the methylene at position 5 of $PGI_2$ (i.e. 9-deoxy-9α,6-nitrilo-5-thia-$PGF_{1\alpha}$) is known. However, it has not been reported that prostacyclin compounds have an activity useful in treatment of cataract.

As a result of extensive studies about the biological properties of compounds having natural and synthetic prostacyclin, the present inventor has discovered that these compounds are useful as an agent for treating cataract.

SUMMARY OF THE INVENTION

In a first aspect, the present invention provides a method for treatment of cataract which comprises administering, to a subject in need of such treatment, a prostacyclin compound in an amount effective in treatment of cataract.

In a second aspect, the present invention provides a use of a prostacyclin compound for the manufacture of a medicament for treatment of cataract.

In a third aspect, the present invention provides a pharmaceutical composition for treatment of cataract comprising a prostacyclin compound in association with a pharmaceutically acceptable carrier, diluent or excipient.

DETAILED DESCRIPTION OF THE INVENTION

Cataract is a disease characterized by an opacity of the crystalline lens of the eye. As used herein, the term "cataract" includes precataract which can be observed as an increase in intensity of scattered light in the crystalline lens, coloring of the crystalline lens, hardening of a nucleus of lens etc. According to the invention, the prostacyclin compounds can be used in all the cataract, particularly in prophylaxis, i.e. prevention or inhibition of onset of cataract, regardless of its cause. Examples of cataract include senile cataract, traumatic cataract, nutritional cataract, diabetic cataract, toxic cataract, radiation cataract, etc.

As used herein, the term "treatment" or "treating" refers to any means of control of a disease in a mammal, including preventing the disease, curing the disease, relieving the disease and arresting or relieving the development of the disease.

As stated above, prostacyclin is another name of $PGI_2$. The term "prostacyclin compounds" herein, however, includes any compounds formed by cyclizing between positions 6 and 9 of the prostanoic acid with the interposition of one atom (e.g. C, O, S, N, etc), and their substituted compounds or derivatives irrespective of the number of double bond, the presence of hydroxyl group or other substituent and any change in chain moieties.

Nomenclature

Nomenclature of prostacyclin compounds herein uses the numbering system of PGI represented in Formula (B) which in turn is based on the numbering system of prostanoic acid represented in formula (A) shown above.

While formulas (A) and (B) show basic skeletons having twenty carbon atoms, the prostacyclin compounds used in the present invention are not limited to those having the same number of carbon atoms. The carbon atoms in Formula (A) are numbered 2 to 5 on the α-chain and 6,6a (or 9α) and 7 on the ring formed in the formula (B) starting from the α-carbon atom adjacent to the carboxylic carbon atom which is numbered 1 and towards the five-membered ring, 8 to 12 on the ring common in the formulas (A) and (B) starting from the carbon atom on which the α-chain in the formula (A) is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of the above formulas unless otherwise specified. For example, a $PGI_2$ compound saturated between positions 13 and 14, having an oxo group in place of the hydroxy group at position 15 and a carbon atom (as $CH_2$) in place of oxygen atom at position 6a(9α) is nominated as 13,14-dihydro-15-keto-6a-carba-$PGI_2$ (or 13,14-dihydro-15-keto-9(O)-methano-$PGI_2$).

As stated above, nomenclature of the prostacyclin compounds is based upon the structure of PGI. These compounds, however, can also be named according to the IUPAC naming system. For example, the above exemplified compound is named as [3aS-[2E,3aα,4α(-1E,3R*),5β,6aα]]-5-[hexahydro-5-hydroxy-4-(3-oxooctyl)-2(1H)-pentalenylidene]pentanoic acid.

Preferred Compounds

Examples of substitution products or derivatives include esters at the carboxy group at the alpha chain, pharmaceutically or physiologically acceptable salts, unsaturated derivatives having a double bond bond between positions 2 and 3, positions 5 and 6, positions 6 and 6a (or 9a) or positions 6 and 7, or a single bond between positions 5 and 6, respectively, substituted derivatives having substituent(s) on carbon atom(s) at position 3, 5, 6, 16, 17, 19 and/or 20, compounds having substituents such as lower alkyl, aryl and aralkyl at position 6a (or 9α) when the atom at this position is a nitrogen atom and compounds having lower alkyl or a hydroxy (lower) alkyl group at position 11 in place of the hydroxy group, of the above PGs.

Examples of substituents present in preferred compounds are as follows: Substituents on the carbon atom at position 3, 17 and/or 19 include lower alkyl, for example, $C_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 17 include halogen atom e.g. chlorine, fluorine etc. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g. $C_{1-4}$ alkoxy-$C_{1-4}$ alkyl. Substituents on the carbon atom at position 5 include halogen atom e.g. chlorine, fluorine etc. Substituents on the nitrogen atom at position 6a (or 9α) include $C_{1-4}$ alkyl, $C_{6-12}$ aryl and $C_{7-13}$ aralkyl of compounds having hydroxy, lower alkyl or hydroxy(lower) alkyl substituent on the carbon atom at position 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 16, those having a halogen atom e.g. chloro, fluoro etc. at position 17, those having a lower alkyl e.g. methyl, ethyl etc. at position 19, those having a halogen atom e.g. chlorine, fluorine etc. at position 5, those having a lower alkyl on the nitrogen atom at position 6a (or 9α, those having a lower alkyl, e.g. methyl, ethyl, etc. at position 20 and those having phenyl or phenoxy which are optionally substituted with halogen or haloalkyl at position 16 in place of the rest of the alkyl chain.

A group of preferred compounds used in the present invention has the formula

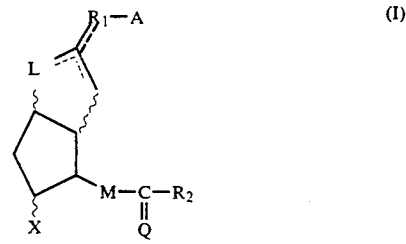

wherein the symbol of a line with a dotted line is a single bond or a double bond provided that only one of the three symbols can be a double bond, X is hydrogen, hydroxy, halo, lower alkyl, or hydroxy(lower)alkyl, A is —$CH_2OH$, —$COCH_2OH$, —COOH or its functional derivative, L is oxygen, carbon, sulfur or nitrogen atom, M is —$CH_2$—$CH_2$, —CH=CH— or —C≡C—, Q is oxo,

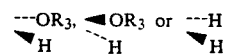

wherein $R_3$ is hydrogen or lower alkyl, $R_1$ is bivalent saturated or unsaturated, lower or medium aliphatic hydrocarbon residue, which is unsubstituted or substituted with halogen, hydroxy, oxo, lower alkoxy, lower alkanoyloxy, cyclo(lower)alkyl, aryl or aryloxy, $R_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

In the above formula, the term "unsaturated" in the definitions for $R_1$ and $R_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double bond at position 5.

It is preferred that the group —CH=CH— in M has the trans configuration.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 6 to 12 carbon atoms for $R_2$.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy(lower)alkyl, monocyclic aryl(lower) alkyl, monocyclic aroyl(lower)alkyl or halo(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group loweralkyl-O- wherein lower alkyl is as defined above.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

The term "functional derivative" of carboxy as Z includes salts (preferably pharmaceutically acceptable salts), esters and amides.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyethyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

Preferred examples of A include —COOH, —COOCH$_3$, —COOCH$_2$CH$_3$, —COOCH(CH$_3$)$_2$ and —CONHSO$_2$CH$_3$.

The configuration of the ring and the $\alpha$- and/or omega chain in the above formula (I) may be the same as or different from that in the primary PGs. However, the present invention also includes a mixture of a compound having a primary configuration and that of an unprimary configuration.

When the prostacyclin compounds of the present invention have a saturated bond between positions 13 and 14 and an oxo group at position 15, these compounds may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publications (unexamined) No. A-131446/1990 and 178252/1990.

Alternatively, these compounds may be prepared by a process analogous to that described herein or to known processes.

A practical preparation of the prostacyclin compounds involves the following steps. Referring to the Synthetic Scheme I commercially available (1S,5S,6R,7R)6-(trialkylsiloxymethyl)-3-formyl-7-tetrahydropyranyloxybicyclo[3.3.0]oct-2-ene (aldehyde compound (1)) is reacted with an ylide which is separately prepared from (3-carboxypropyl)triphenylphosphine bromide and potassium t-butoxide, and then the product is reacted with diazomethane to give an ester (2). The ester (2) is treated with tetra n-butylammonium fluoride to remove the silyl group to yield the alcohol (3). This alcohol (3) is subjected to Collins oxidation to give the aldehyde (4), which is then reacted with an anion prepared from dimethyl (2-oxo-3-substituted-heptyl)phosphonate and sodium hydride so as to introduce $\omega$-chain. The double bond in the $\omega$-chain is hydrogenated in the presence of palladium/carbon and the like under hydrogen atmosphere. In this process a double bond in the ring remains untreated. The tetrahydropyranyl group, a protective group, is removed with an acid to give an ester (7). An acid corresponding to the ester (7) can be obtained by hydrolysis of the ester (7)

according to the conventional method. Though as an example of phosphonates which can be used for introduction of ω-chain having a fluorine atom at 3-position as a substituent is illustrated in the Example 1, this substituent may be a halogen such as a chlorine atom; or others such as a methyl, ethyl, phenyl, benzyl, hydroxyl, methoxy or ethoxy group and the like.

The compounds having a double bond between $C_{13}$–$C_{14}$ can be prepared according to a process illustrated by the Synthetic Scheme II. In this process the ester (2) which can be prepared according to the same manner as in the Scheme I is hydrogenated in the presence of palladium/carbon under hydrogen atmosphere to give 4-carbomethoxybutyl compounds (2'). This compound (2') is treated with tetra n-butylammonium fluoride to remove the silyl group to yield the alcohol (3'). This alcohol (3') is subjected to Collins oxidation to give the aldehyde (4'), which is then reacted with an anion which is prepared from dimethyl(2-oxo-3-substituted-heptyl)phosphonates and sodium hydride to introduce ω-chain to give the 15-keto compound (5'). The tetrahydropyranyl group, a protective group, is removed with an acid to give an ester (7'). An acid corresponding to the ester (7') can be obtained by hydrolysis of the ester (7') according to the conventional method. Though as an example of phosphonates which can be used for introduction of ω-chain one having a fluorine atom at 3-position as a substituent is illustrated in the Example 4, this substituent may be a halogen atom such as a chlorine atom; or other groups such as a methyl, ethyl, phenyl, benzyl, hydroxyl, methoxy or ethoxy group and the like.

16,16-Difluoro compound (9) can be prepared by reacting an anion derived from dimethyl(2-oxo-3,3-difluoroheptyl)phosphonate with the aldehyde (4') as illustrated in the Synthetic Scheme III.

13,14-Dihydro-PGI$_2$s can be prepared according to the Synthetic Scheme IV. The compound (5) which can be prepared according to the same manner as illustrated in the Scheme [I] can be hydrogenated using tricarbonyl chromium methyl benzoate complex (refer to Japanese Patent Application KOKAI No.61-37740) (in this case the two double bonds on the α-chain and in the ring, which conjugate each other are also hydrogenated to one double bond between the carbon atoms combining the ring and the α-chain). The obtained compound is treated with an acid to remove the tetrahydropyranyl group to yield an ester (15'). Alternatively, the compound (11) obtained in the above process is reduced with sodium borohydride to an alcohol, and then the alcohol is hydrolyzed with an alkali to give a carboxylic acid (13). The carboxylic acid (15) can be obtained by removing the tetrahydropyranyl group by hydrolysis after Jones oxidation. In the Scheme IV a fluorine atom is shown as a substituent on the carbon atom adjacent to the carbonyl group, but another substituent as explained hereinbefore may be used.

The compounds can be prepared from the compound (5) which can be obtained according to the processes illustrated in the Synthetic Scheme V. The carbonyl group of the compound (5) is reduced using sodium borohydride to give a 15-hydroxy compound (5''), which is then hydrogenated using tricarbonyl chromium benzoic acid methyl complex (see Japanese Patent Application KOKAI No. 61-37740) (in this case two double bonds on the α-chain and in the ring, which conjugates each other are also hydrogenated to one double bond between the carbon atoms bonding the ring and the α-chain).

The obtained compound (12) was hydrolyzed with alkali to an acid (13'), which is then oxidized by Jones oxidation to give a ketone (14'). From the ketone (14') is removed the tetrahydropyranyl group by an acid to yield the desired carboxylic acid (15'). The substituent(s) on the carbon atom adjucent to the carbonyl group may be other atom(s) or group(s) as aforementioned.

16,16-Difluoro compound (21) can be prepared by reacting an anion derived from dimethyl(2-oxo-3,3-difluoroheptyl)phosphonate with aldehyde (4) as illustrated in the Synthetic Scheme VI.

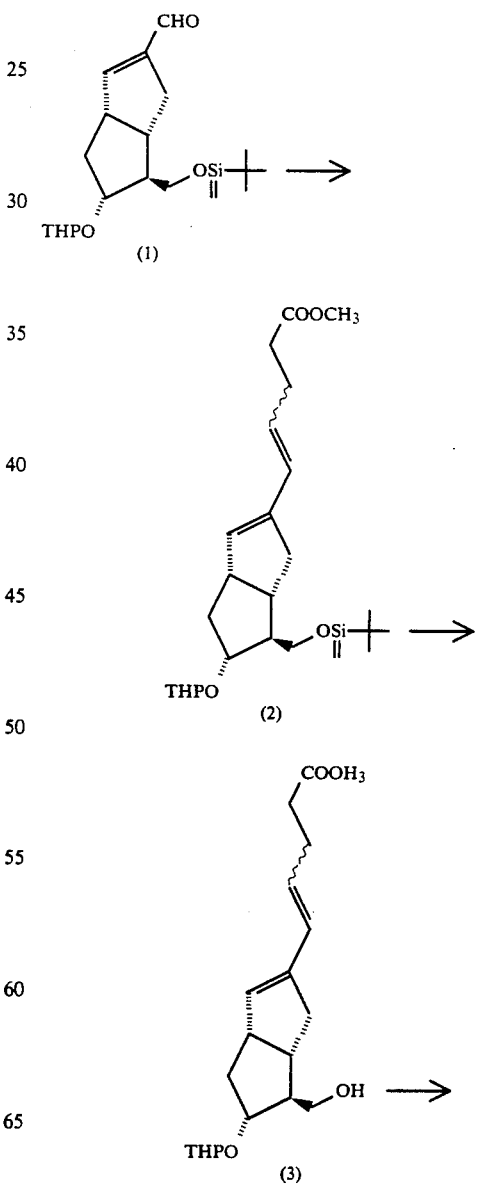

Synthetic Scheme I

-continued
Synthetic Scheme I
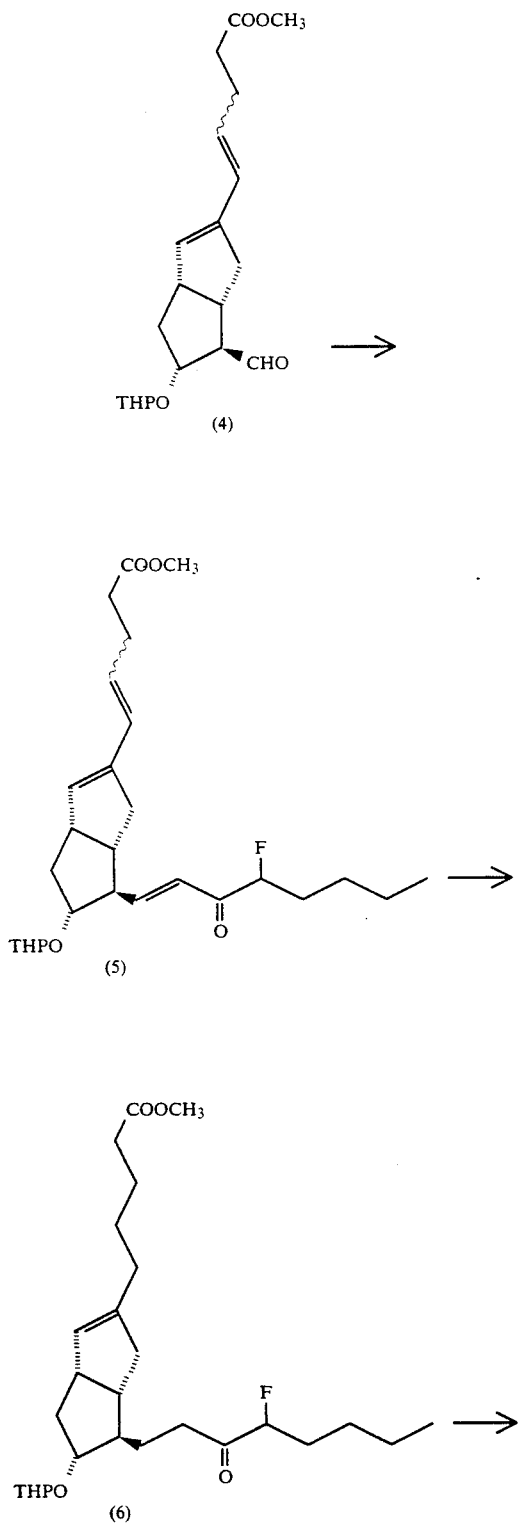
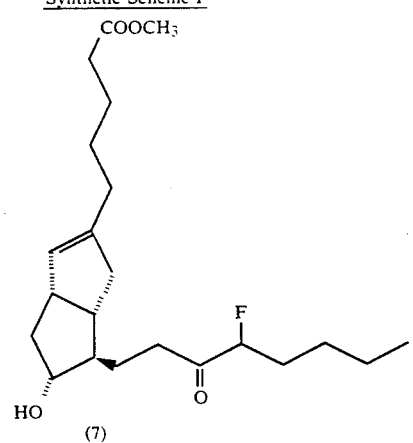
Synthetic Scheme II
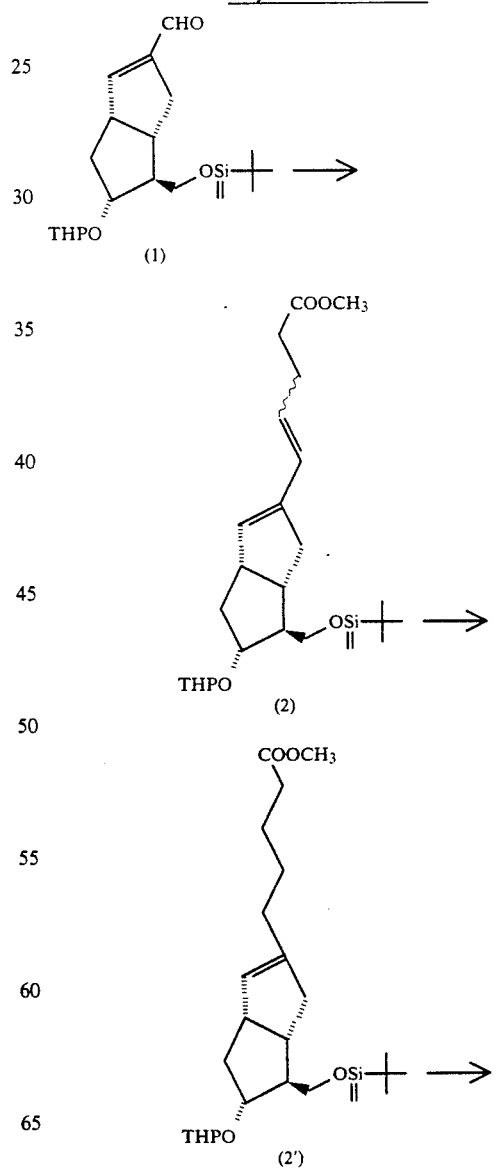

-continued
Synthetic Scheme II
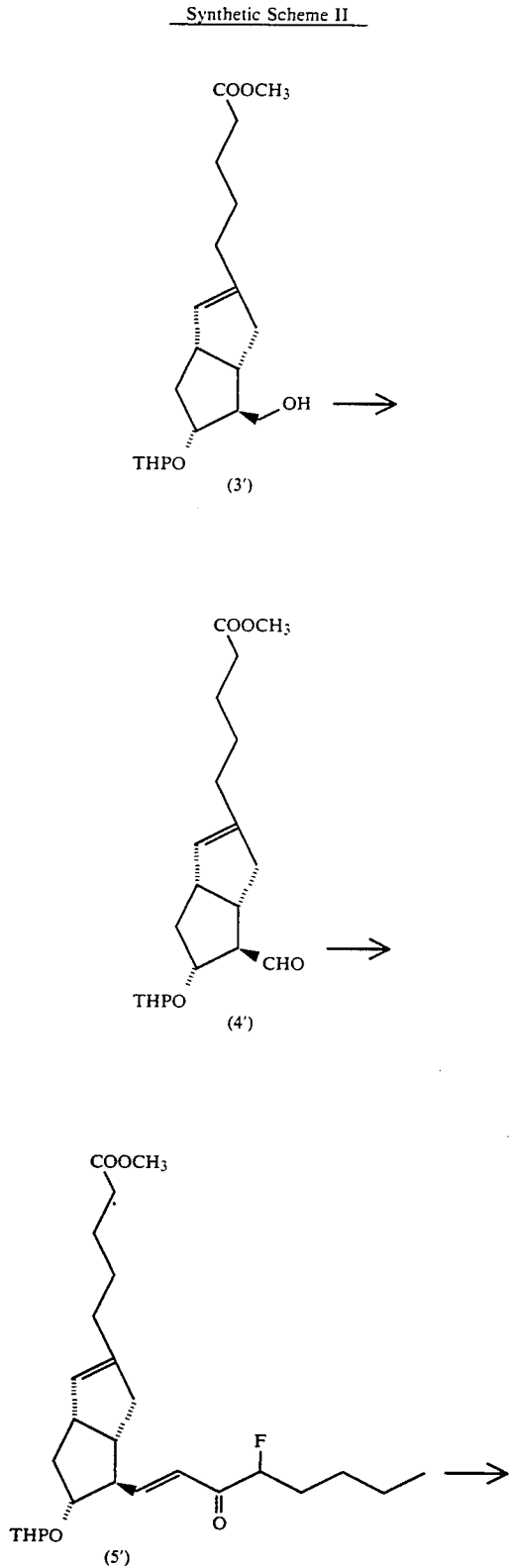
Synthetic Scheme II
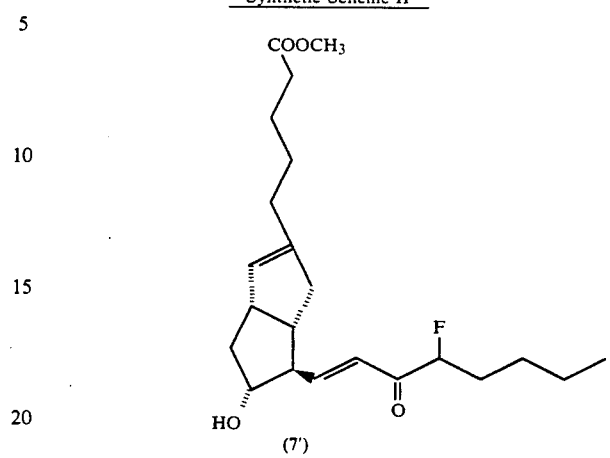
Synthetic Scheme III
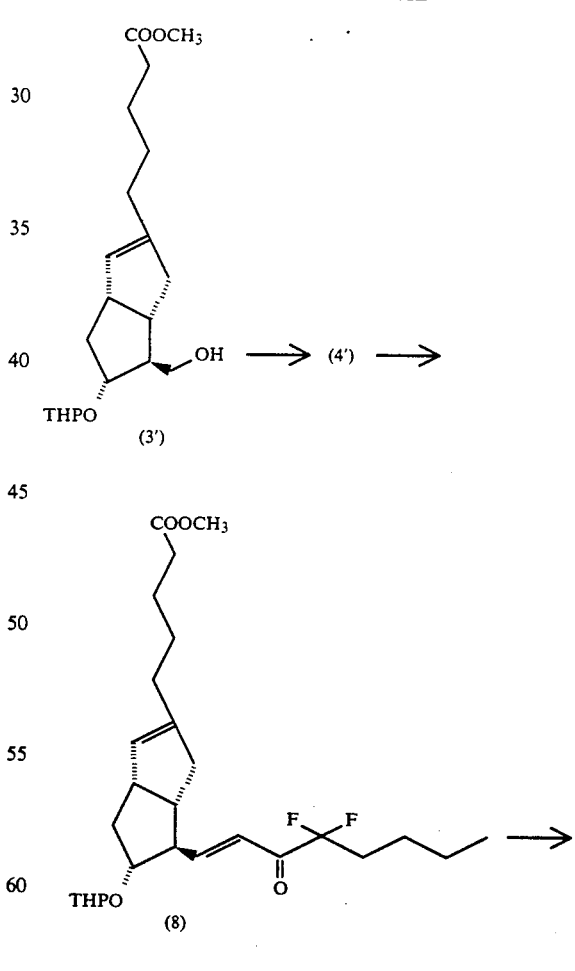

13
-continued
Synthetic Scheme III
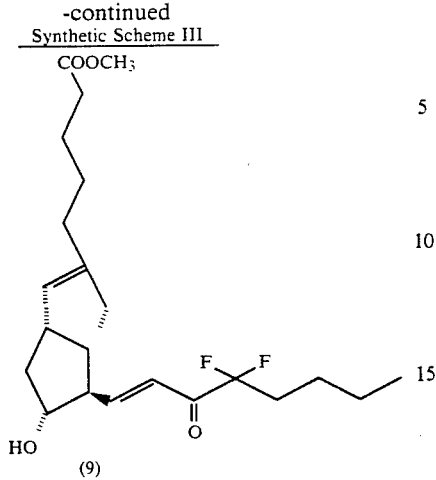
14
-continued
Synthetic Scheme V
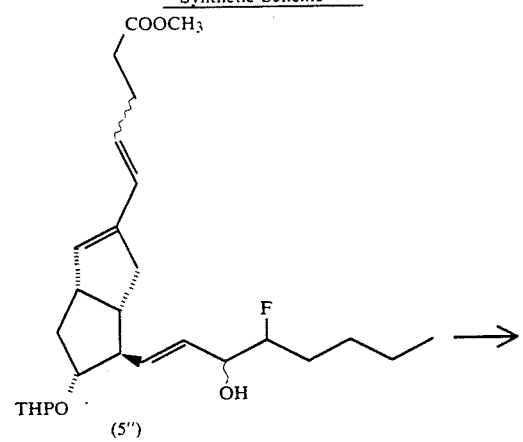
Synthetic Scheme IV
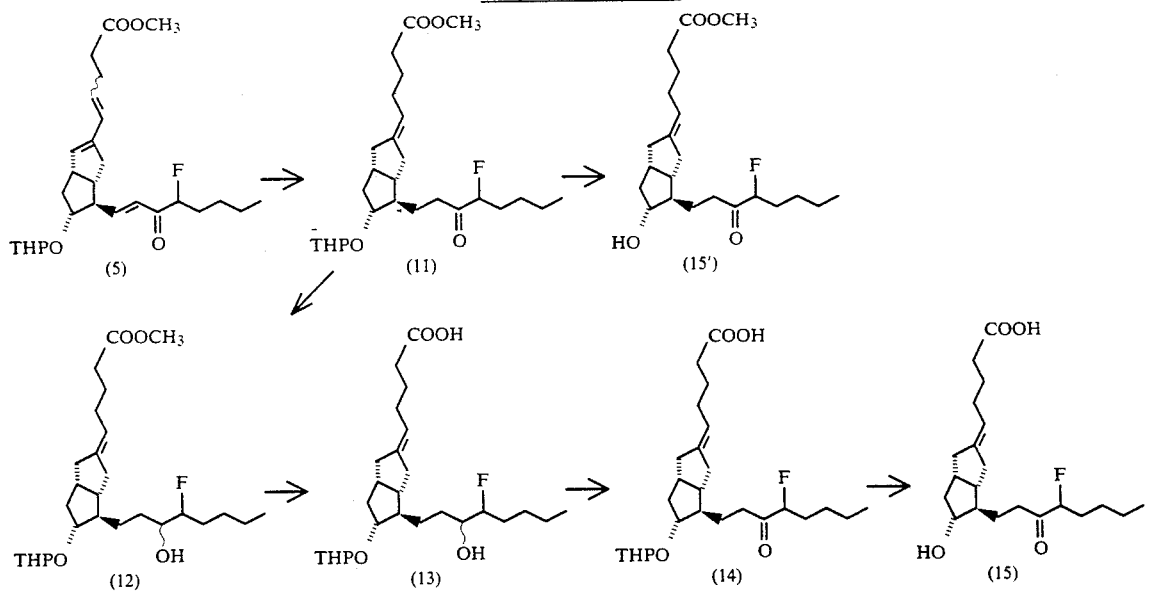
Synthetic Scheme V
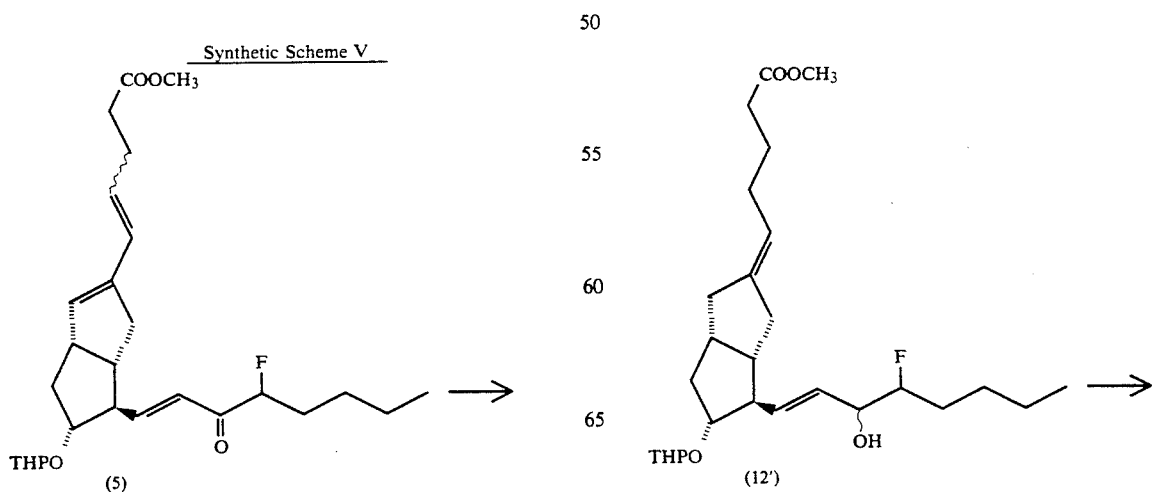

-continued
Synthetic Scheme V
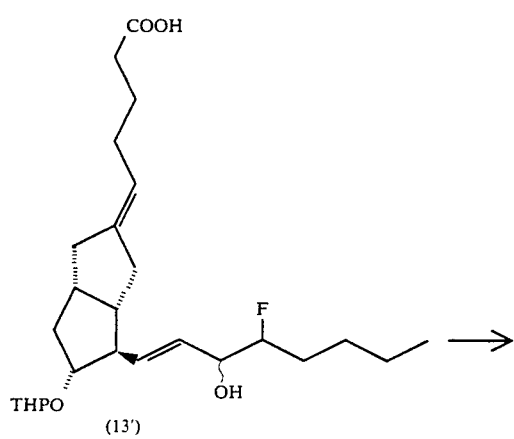
(13')
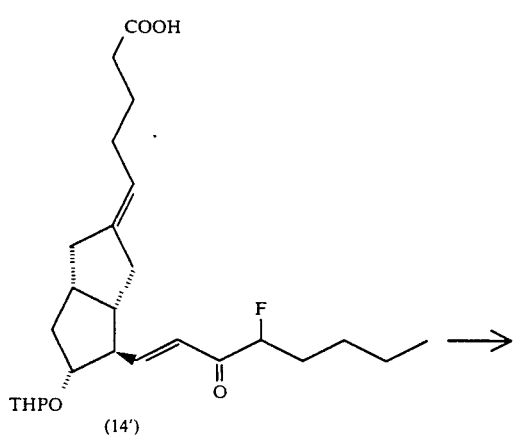
(14')
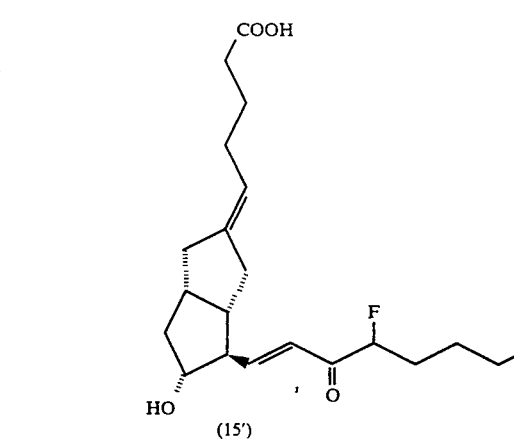
(15')
Synthetic Scheme VI
(3) ⟶ (4) ⟶
-continued
Synthetic Scheme VI
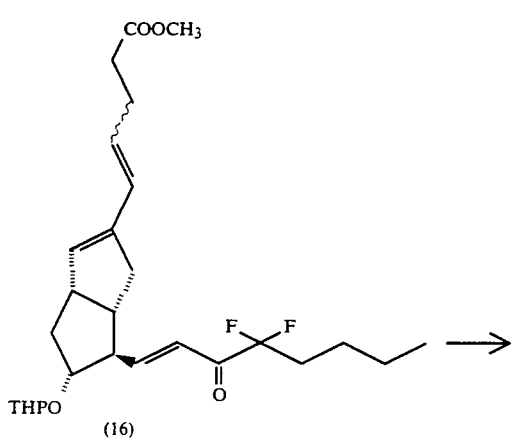
(16)
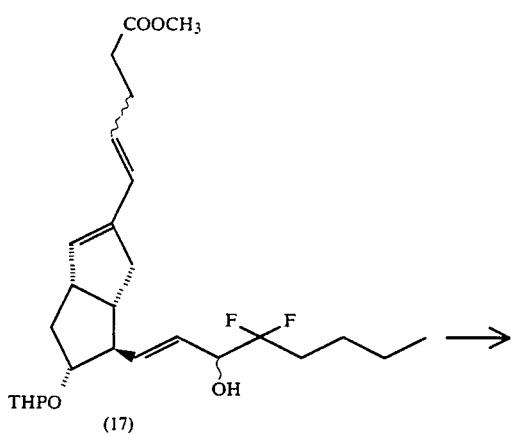
(17)
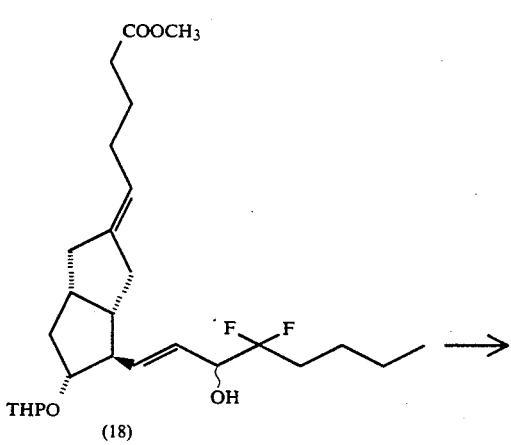
(18)

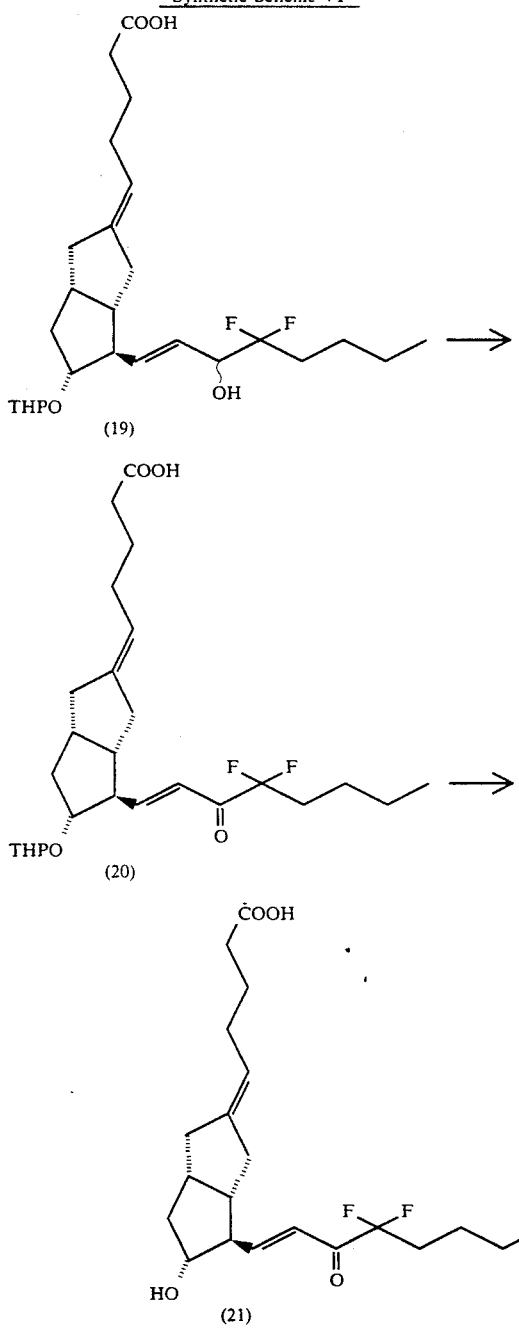

-continued
Synthetic Scheme VI treatment and the like, satisfactory effects will be obtained with the dosage of 0.01–100 μg/eye administered locally or 0.001–500 mg/kg administered systemically in 2 to 4 divided doses a day or as a sustained form.

The ophthalmic composition used according to the invention includes ophthalmic solution, ophthalmic ointment and the like. The ophthalmic solution can be prepared by dissolving an active ingredient in a sterile aqueous solution such as a physiological saline or a buffered solution, or as a combination of a solid and a solution for dissolving said solid to make a ready-to-use preparation. The ophthalmic ointment can be prepared by mixing an active ingredient with an ointment base.

The solid composition for oral administration used according to the invention includes tablets, troches, buccals, capsules, pills, powders, granules and the like. The solid composition contains one or more active substances in admixture with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives, in addition to the inactive diluent, for example, lubricants e.g., magnesium stearate, a disintegrator e.g. cellulose calcium gluconates, stabilizers e.g. α-, β- or δ-cyclodextrins, etherated cyclodextrins (e.g. dimethyl-α-, dimethyl-β-, trimethyl-β-, or hydroxypropyl-β-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediate effect is desired. For this purpose, base e.g. glycerine, lactose may be used.

Liquid compositions for oral administration include pharmaceutically acceptable emulsions, solutions, suspensions, syrups, elixirs and the like and contain a commonly used inactive diluent e.g. purified water or ethyl alcohol. The composition may contain additives e.g. wetting agents, suspending agents, sweeteners, flavors, perfumes and preservatives.

The composition of the present invention may be in the form of sprays which may contain one or more active ingredients and which can be prepared according to a well known methods.

Since the compounds used in the present invention have an activity useful for preventing or curing cataract, these can be used for preparing a medicament for treating cataract. Such activities can be measured by the standard methods such as galactose-induced cataract of rats.

The compounds used in the present invention may be used as a medicine for animals and human beings and usually applied systemically or locally by such methods as ophthalmic administration, oral administration, intravenous injection (including instillation), subcutaneous injection, suppository and the like. While the dosage will vary depending on the particular animal or human patient, age, body weight, symptom to be treated, desired therapeutic effect, administration route, term of An injection of this invention for non-oral administration includes sterile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of 13,14-dihydro-15-keto 16(RS)-fluoro-6,6a-dehydro-6a-carba-$PGI_1$ methyl ester (13,14-dihydro-15-keto-16(RS)-fluoro-9 (O)-methano -$\Delta^{6(9\alpha)}$-$PGI_1$ methyl ester)

1-1 Synthesis of (1S,5S,6S,7R)-6-(t-butyldimethylsiloxymethyl)-3-[4-methoxycarbonyl -1(EZ)-butenyl]-7-tetrahydropyranyloxy-bicyclo[3.3.0]oct-2-ene (2):

Commercially available (1S,5S,6S,7R)-6-(t-butyl-dimethylsiloxymethyl)-3-formyl -7-tetrahydropyranyloxybicyclo[3.3.0]oct-2-ene (1.00 g) (1) was reacted with an ylide which was prepared from (3-carboxypropyl)triphenylphosphine bromide and potassium t-butoxide. A crude carboxylic acid was obtained according to a usual work-up. The product was reacted with diazomethane in ether. A crude product obtained after a usual work-up was purified on a column chromatography (hexane/ethyl acetate=10/1) to give (1S,5S,6S,7R)-6-(t-butyldimethylsilyloxymethyl)-3-[4-methoxycarbonyl-1(EZ)-butenyl]-7-tetrahydropyranyloxybicyclo[3.3.0]oct-2-ene (2) as a colorless oily product. Yield: 0.85 g (67%)

$^1$H NMR ($CDCl_3$) $\delta$0.05 (6H,s), 0.90 (9H,s), 1.05–1.95 (10H,m), 2.10–3.13 (7H,m), 3.27–4.22 (5H,m), 3.63 (3H,s), 4.45–4.69 (1H,m), 5.05–5.65(2H,m), 5.97 (0.67H,d, J=12 Hz), 6.22 (0.33H, d, J=16 Hz)

1-2 Synthesis of (1S,5S,6S,7R)-3-[4-methoxycarbonyl-1(EZ)-butenyl]-6-hydroxymethoxxy-7-tetrahydropyranyloxy-bicyclo[3.3.0]oct-2-ene (3):

(1S,5S,6S,7R)-6-(t-Butyldimethylsiloxymethyl)-3-[4-methoxycarbonyl-1(EZ)-butenyl]-7-tetrahydropyranyloxybicyclo[3.3.0]oct-2-ene (2) obtained in 1-1 (0.85 g) was dissolved in THF. Into the solution, tetra-n-butylammonium fluoride in THF (1.1 M, 6.43 ml) was added, and the mixture was stirred for 18 hours. A crude product obtained after a usual work-up was purified on column chromatography (hexane/ethyl acetate=1/1) to give (1S,5S,6S,7R)-3-[4-methoxycarbonyl-1(EZ)-butenyl]-6-hydroxymethyl-7-tetrahydropyranyloxy-bicyclo[3.3.0]oct-2-ene (3) as a colorless oily product. Yield : 0.59 g (96%)

$^1$H NMR ($CDCl_3$) $\delta$ 1.18–1.93(10H,m), 2.16–3.28(8H,m), 3.42–4.07(5H,m), 3.63(3H, s), 4.55–4.64(0.5H,m), 4.66–4.77(0.5H,m), 5.33(0.67H, dt, J =7.5 Hz, J=12.5 Hz), 5.42–5.67(1.33H,m), 5.99(0.67H,d,J =12.5 Hz), 6.26(0.33H,d,J=15.5 Hz).

1-3 Synthesis of (1S,5S,6S,7R)-3-[4-methoxycarbonyl-1(EZ)-butenyl]-6-[4(RS)-fluoro-3-oxo-(E)-1-octenyl]-7-tetrahydropyranyloxy-bicyclo[3.3.0]oct-2-ene (5):

(1S,5S,6S,7R)-3-[4-Methoxycarbonyl-1(EZ)-butenyl]-6-hydroxymethyl-7-tetrahydropyranyloxy-bicyclo[3.3.0 oct-2-ene (3) (0.240 g) was subjected to Collins oxidation in methylene chloride at 0° C. Into the reaction mixture was added sodium hydrogen sulfonate, and the mixture was filtered. A crude aldehyde (4) obtained after concentration under reduced pressure of the filtrate was dissolved in THF, and reacted with an anion which was prepared from dimethyl (2-oxo-3-fluoroheptyl) phosphonate (0.61 g) and sodium hydride with stirring at 50° C. for 5 hours. The reaction mixture was neutralized with acetic acid. A crude product obtained after a usual work-up was purified on column chromatography (hexane/ethyl acetate=6/1) to give (1S,5S,6S,7R)-3-[4-methoxycarbonyl-1(EZ)-butenyl]-6-[4(RS)-fluoro-3-oxo-( E)-1-octenyl]-7-tetrahydropyranyloxybicyclo[3.3.0]oct-2-ene (5) as a pale yellow oily product. Yield: 0.250 g (85%)

$^1$H NMR($CDCl_3$)$\delta$ 0.70–1.07(3H,m), 1.06–2.14(15H,m), 2.15–4.16(11H,m), 3.66(3H,s), 4.43–4.72(1.5H,m), 4.96–5.71(2.5H,m), 5.95(0.67H,d,J=11 Hz), 6.24(0.33H,d,J=16HZ), 6.36–6.73(1H,m), 6.83–7.23(1H,m).

1-4 Synthesis of (1S, 5S, 6R,7R)-3-(4-methoxycarbonylbutyl)-6-[4(RS)-fluoro-3-oxooctyl]-7-tetrahydropyranyloxy-bicyclo[3.3.0]oct-2-ene (6):

(1S,5S,6S,7R)-3-[4-Methoxycarbonyl-1(EZ)-butenyl]-6-[4(RS)-fluoro-3-oxo-(E )-1-octenyl]-7-tetrahydropyranyloxybicyclo[3.3.0]oct-2-ene (5) (0.094 g) was dissolved in ethyl acetate. Into the solution, palladium(5 wt %)/carbon (0.0094 g) was added and the mixture was stirred under reaction mixture was filtered, and the filtrate was evaporated under reduced pressure. Obtained crude product was chromatographed using a silica gel treated with silver nitrate (15 wt %) (hexane/ethyl acetate=12/1−9/1) to give (1S,5S,6R,7R)-3-(4-methoxycarbonyl)-6-[4(RS)-fluoro-3-oxooctyl]- 7-tetrahydropyranyloxybicyclo[3.3.0]oct-2-ene (6) as a pale yellow oily product. Yield: 0.042 g (44%)

$^1$H NMR($CDCl_3$)$\delta$ 0.66–1.03(3H,m), 1.03–3.12(31H,m), 3.24–4.02(3H,m), 3.63(3H,s), 4.27–4.53(0.5H,m), 4.50–4.70(1H,m), 4.83–5.06(0.5H,m), 5.06–5.33(1H,m).

1-5 Synthesis of 13,14-dihydro-15-keto-16(RS)fluoro-6,6a-dehydro-6a-carba-$PGI_1$ methyl ester (13,14-dihydro-15-keto-16(RS)-fluoro-9(O)-methano-$\Delta^{6(9\alpha)}$-$PGI_1$ methyl ester):

(1S,5S,6R,7R)-3-(4-Methoxycarbonylbutyl)-6-[4(RS)-fluoro-3-oxooctyl]-7-tetrahydropyranyloxy-bicyclo[3.3.0]oct-2-ene (6) (0.088 g) was dissolved in a mixture of acetic acid, water and THF (4 : 2 : 1) and the mixture stirred at 45° C. for 4 hours. A reaction mixture was concentrated under reduced pressure, and a crude product obtained was purified on column chromatography (hexane/ethyl acetate=6/1−4/1) to give 13,14-dihydro-15-keto-16(RS)-fluoro-6,6a-dehydro-6a-carba-$PGI_1$ methyl ester (13,14-dihydro-15-keto-16(RS)-fluoro-9(O)-methano-$\Delta^{6(9\alpha)}$-$PGI_1$ methyl ester) (7) as a pale yellow product. Yield: 0.072 g (100%)

$^1$H NMR($CDCl_3$)$\delta$ 0.73–1.05(3H,m), 1.05–3.15(26H,m), 3.46–4.04(1H,m), 3.63(3H,s), 4.33–4.56(0.5H,m), 4.48–5.07(0.5H,m), 5.07–5.36(1H,m).

PREPARATION EXAMPLE 2

Preparation of
13,14-dihydro-15-keto-16(RS)-fluoro-6a-carba-PGI$_2$
(13,14-dihydro-15-keto-16(RS)-fluoro-9(O)-methano-PGI$_2$)

2-1 Synthesis of (1S,2R,3R,5S)-7(E)-(4-methoxycarbonylbutylidene)-2-[4(RS )-fluoro-3-oxooctyl]-3-tetrahydropyranyloxy-bicyclo[3.3.0]octane (11):

(1S,5S,6S,7R)-3-[4-Methoxycarbonyl-1(EZ)-butenyl]-6-[4(RS)-fluoro-3-oxo-(E )-1-octenyl]-7-tetrahydropyranyloxybicyclo[3.3.0]oct-2-ene (5) (0.109 g) was dissolved in acetone in an autoclave. Into the solution, a tricarbonyl chromium/methyl benzoate complex (0.023 g) was added. The mixture was degassed and the content was stirred under a hydrogen atmosphere (70 kg/cm$^2$) at 125° C. for 20 hours. The reaction mixture was concentrated under reduced pressure. A crude product obtained was chromatographed (hexane/ethyl acetate=10/1−7/1 to give (1S,2R,3R,5S)-7(E)-(4-carbomethoxybutylidene)-2-[4(RS )-fluoro-3-oxo-octyl]-3-tetrahydropyranyloxy-bicyclo[3.3.0]octane (11) as a colorless oily product. Yield: 0.157 g (99%)

$^1$H NMR(CDCl$_3$)δ 0.76~1.05(3H,m), 1.05~2.91(31H,m), 3.27~3.98(3H,m), 3.62(3H,s), 4.31~4.72(1.5H,m), 4.79~5.32(1.5H,m).

2-2 Synthesis of (1S,2R,3R,5S)-7(E)-(4-methoxycarbonylbutylidene)-2-[4(RS )-fluoro-3(RS)-hydroxyoctyl]-3-tetrahydropyranyloxybicyclo[3.3.0]octane (12):

(1S,2R,3R,5S)-7(E)-(4-Methoxycarbonylbutylidene)-2-[4(RS)-fluoro-3-oxooctyl]-3 -tetrahydropyranyloxybicyclo[3.3.0]octane (11) (0.197 g) was dissolved in methanol. To the solution, a sodium borohydride (0.017 g) was added at 0° C. The mixture was stirred for 30 minutes and treated in the conventional manner. A crude product obtained was chromatographed (hexane/ethyl acetate=3/1) to give (1S,2R,3R,5S)-7(E)-(4-methoxycarbonylbutylidene)-2-[4(RS)-fluoro-3(RS )-hydroxy-octyl-3-tetrahydropyranyloxybicyclo[3.3.-0]octane (12). Yield: 0.185 g (93%)

$^1$H NMR(CDCl$_3$)δ 0.72~1.05(3H,m), 1.05~2.66(32H,m), 3.22~4.15(4.5H,m), 3.62(3H,s), 4.42~4.67(1.5H,m), 5.00~5.31(1H,m).

2-3 Synthesis of (1S,2R,3R,5S)-7(E)-(4-Carboxybutylidene)-2-[4(RS)-fluoro-3 (RS)-hydroxyoctyl]-3-tetrahydropyranyloxybicyclo[3.3.0]octane (13):

(1S,2R,3R,5S)-7(E)-(4-Methoxycarbonylbutylidene)-2-[4(RS)-fluoro-3(RS)-hydroxy-octyl ]-3-tetrahydropyranyloxybicyclo[3.3.0]octane (12) (0.185 g) was dissolved in methanol. To the solution, an aqueous solution of 1N sodium hydroxide (6.5 ml) was added. The mixture was stirred at room temperature for 4 hours. After a usual work-up a crude product (1S,2R,3R,5S)-7(E)-(4-carboxybutylidene)-2-[4(RS)fluoro-3(RS )-hydroxyoctyl]-3-tetrahydropyranyloxybicyclo[3.3.0]octane (13) was obtained. Yield: 0.184 g 2-4 Synthesis of (1S,2R,3R,5S)-7(E)-(4-carboxybutylidene)-2-[4(RS)-fluoro-3 -oxooctyl]-3-tetrahydropyranyloxybicyclo[3.3.0]octane (14):

(1S,2R,3R,5S)-7(E)-(4-Carboxybutylidene)-2-[4(RS)-fluoro-3(RS)-hydroxyoctyl]-3 -tetrahydropyranyloxybicyclo[3.3.0]octane (13) (0.184 g) was oxidized with Jones reagent between about −15° and −5° C. After stirring for 40 minutes, isopropyl alcohol (0.43 ml) was added, and the mixture was treated by a usual work-up. Obtained crude product was purified on column chromatography (hexane/ethyl acetate=15/1−10/1) using silica gel treated with an acid (CC-4: available from Mallinckrodt Co., Ltd.) to give (1S,2R,3R,5S)-7(E)-(4-carboxybutylidene)-2-[4(RS)-fluoro-3-oxooctyl]-3-tetrahydropyranyloxybicyclo[3.3.0]octane (14) as a colorless oily product. Yield: 0.072 g (40%)

$^1$H NMR(CDCl$_3$)δ 0.72~1.04(3H,m), 1.04~2.88(31H,m), 3.20~3.98(3H,m), 4.20~4.68(1.5H,m), 4.75~5.33(1.5H,m), 6.52~8.52(1H,brs).

2-5 Preparation of 13,14-dihydro-15-keto-16(RS)-fluoro-6a-carba-PGI$_2$ (13,14-dihydro-15-keto-16(RS)-fluoro-9(O)-methano-PGI$_2$) (15):

(1S,2R,3R,5S)-7(E)-(4-Carboxybutylidene)-2-[4(RS)-fluoro-3-oxooctyl]-3-tetrahydropyranyloxybicyclo[3,3,0]-octane (14) (0.070 g) was dissolved in a mixture of acetic acid, water and THF (4 : 2 : 1) and the mixture was stirred at 45° C. for 3.5 hours. The reaction mixture was concentrated under reduced pressure. A crude product obtained was purified on column chromatography (hexane/ethyl acetate=3.5/1) using a silica gel (CC-4) to give 13,14-dihydro-15-keto-16(RS)-fluoro-6a-carba-PGI $_2$ (13,14-dihydro-15-keto-16(RS)-fluoro-9(0)-methano-PGI$_2$) (15) as a colorless oily product. Yield: 0.048 g (84%)

$^1$H NMR(CDCl$_3$)δ 0.65~1.05(3H,m), 1.05~2.85(25H,m), 3.43~3.82(1H,m), 4.26~4.57(0.5H,m), 4.76~5.35(1.5H,m), 5.20~6.57(2H,brs).

PREPARATION EXAMPLE 3

Preparation of
13,14-dihydro-15-keto-16(RS)-fluoro-a-carba-PGI$_2$ methyl ester
(13,14-dihydro-15-keto-16(RS)-fluoro-9(O)-methano-PGI$_2$ methyl ester) (15′)

(1S,2R,3R,5S)-7(E)-(4-Methoxycarbonylbutylidene)-2-(RS)-fluoro-3-oxo-octyl]-3-tetrahydropyranyloxybicyclo[3.3.0]octane (11) (0.070 g) was dissolved in a mixture of acetic acid, water and THF (4 : 2 : 1), and the mixture was stirred at 45° C. for 3 hours. The reaction mixture was concentrated under reduced pressure, and crude product obtained was purified on column chromatography (hexane/ethyl acetate=3.5/1) to give 13,14-dihydro-15-keto-16(RS)-fluoro-6a-carba-PGI$_2$ methyl ester (13,14-dihydro-15-keto-16(RS)-fluoro-9(O)-methano-PGI$_2$ methyl ester) (15′) as a colorless oily product. Yield: 0.038 g (67%)

$^1$H NMR(CDCl$_3$) δ 0.75~1.05(3H,m), 1.05~2.87(26H,m), 3.37~3.96(1H,m), 3.64(3H,s), 4.28~4.53(0.5H,m), 4.77~5.32(1.5H,m).

PREPARATION EXAMPLE 4

Preparation of
16(RS)-fluoro-15-keto-6,6a-dehydro-6a-carba-PGI$_1$ methyl ester
(16(RS)-fluoro-15-keto-9(O)-methano-Δ$^{6(9\alpha)}$-PGI$_1$ methyl ester)

4-1 Synthesis of (1S,5S,6S,7R)-6-(t-butyldimethylsiloxymethyl)-3-[4 -methoxycarbonyl-1(EZ)butenyl]-7-tetrahydropyranyloxy-bicyclo[3.3.0]oct-2-ene (2):

In the same manner as in the Example 1, 1-1 the title compound (2) was prepared.

4-2 Synthesis of (1S,5S,6S,7R)-6-(t-butyldimethylsiloxymethyl)-3-(4-methoxycarbonylbutyl-7-tetrahydropyranyloxybicyclo[3.3.0]octo-2-ene (2′):

(1S,5S,6S,7R)-6-(t-Butyldimethylsiloxymethyl)-3-[4-methoxycarbonyl-1(EZ)-butenyl]-7-tetrahydropyranyloxybicyclo[3.3.0]oct-2-ene (2) (0.214 g) was dissolved in methanol. To the solution, palladium (10%)/carbon (0.050 g) was added, and the mixture was stirred under hydrogen atmosphere at room temperature for 45 minutes. The reaction mixture was filtered and the filtrate was concentrated under reduced pressure. A crude product was chromatographed (hexane/ethyl acetate=40/1−30/1) using silica gel treated with silver nitrate (10 wt. %) to give (1S,5S,6S,7R)-6-(t-butyldimethylsiloxymethyl)-3-(4-carbomethoxybutyl)-7-tetrahydropyranyloxybicyclo[3.3.0]octo-2-ene (2') as a colorless oily product. Yield: 0.151 g (70%)

$^1$H NMR(CDCl$_3$)δ 0.05(6H,s), 0.88(9H,s), 0.97∼3.03(21H,m), 3.23∼4.15(5H,m), 3.62(3H,s), 4.45∼4.69(1H,m), 5.10∼5.33(1H,m).

4-3 Synthesis of (1S,5S,6S,7R)-3-(4-methoxycarbonylbutyl)-6-hydroxymethyl-7-tetrahydropyranyloxybicyclo[3.3.0]oct-2-ene (3'):

(1S,5S,6S,7R)-6-(t-Butyldimethylsiloxymethyl)-3-(4-methoxycarbonylbutyl)-7-tetrahydropyranyloxybicyclo[3.3.0]oct-2-ene (2') (0.294 g) was dissolved in THF. Into the solution, tetra-n-butyl-ammonium fluoride solution in THF (1.1M, 2.2 ml) was added, and the mixture was stirred at room temperature for 18 hours. A crude compound obtained after a usual work-up was purified on column chromatography (hexane/ethyl acetate=1/1) to give (1S,5S,6S,7R)-3-(4-carbomethoxybutyl)-6-hydroxymethyl-7-tetrahydropyranyloxybicyclo[3.3.0]octo-2-ene (3') as a colorless oily product. Yield: 0.228 g $^1$H NMR(CDCl$_3$)δ 0.76∼3.13(22H,m), 3.27∼4.13(5H,m), 3.63(3H,s), 4.46∼4.77(1H,m), 5.02∼5.42(1H,m).

4-4 Synthesis of (1S,5S,6S,7R)-3-(4-methoxycarbonylbutyl)-6-[4(RS)-fluoro-3-oxo-(E)-1-octenyl]-7-tetrahydoropyranyloxybicyclo[3.3.0]oct-2-ene (5'):

(1S,5S,6S,7R)-3-(4-Carbomethoxybutyl)-6-hydroxymethyl-7-tetrahydropyranyloxybicyclo[3.3.0]oct-2-ene (3') ((0.125 g) was dissolved in DMSO. To the solution, a solution of triethylamine (0.93 ml) and sulfur trioxide/pyridine complex (0.504 g) in DMSO was added, and the mixture was stirred at room temperature for 1.5 hours. A crude aldehyde (4') obtained after usual work-up was dissolved in THF, and reacted at 50° C. with the anion prepared from dimethyl(2-oxo-3-fluoroheptyl)phosphonate (0.341 g) and sodium hydride. After stirring for 3 hours, the reaction mixture was neutralized with acetic acid. A crude product obtained according to a usual work-up was purified on column chromatography (hexane/ethyl acetate=7/1) to give (1S,5S,6S,7R)-3-(4-methoxycarbonylbutyl)-6-[4(RS)-fluoro-3-oxo-(E)-1-octenyl]-7-tetrahydoropyranyloxybicyclo[3.3.0]oct-2-ene (5'). Yield: 0.088 g (56%)

$^1$H NMR(CDCl$_3$)δ 0.75∼1.06(3H,m), 1.05∼3.14(27H,m), 3.26∼4.13(3H,m), 3.63(3H,s), 4.38∼4.71(1.5H,m), 5.01∼5.43(1.5H,m) 6.26 - 6.68(1H,m), 6.80∼7.26(1H,m).

4-5 Synthesis of 16(RS)-fluoro-15-keto-6,6a-dehydro-6a-carba-PGI$_1$ methyl ester (16(RS)-fluoro-15-keto-9(O)-methano-Δ$^{6(9\alpha)}$-PGI$_1$ methyl ester) (7'):

(1S,5S,6S,7R)-3-(4-Methoxycarbonylbutyl)-6-[4(RS)-fluoro-3-oxo-(E)-1-octenyl ]-7-tetrahydoropyranyloxybicyclo [3.3.0]oct-2-ene (5') (0.088 g) was dissolved in a mixture of acetic acid, water and THF (4 : 2 : 1), and the mixture was stirred at 45° C. for 3 hours. The reaction mixture was concentrated under reduced pressure, and a crude product obtained was purified on column chromatography (hexane/ethyl acetate=3/1) to give 16(RS)-fluoro-15-keto-6,6a-dehydro-6a-carba-PGI$_1$ methyl ester (16(RS)-fluoro-15-keto-9(O)-methano-Δ$^{6(9\alpha)}$-PGI$_1$ methyl ester) (7'). Yield: 0.069 g (96%)

$^1$H NMR(CDCl$_3$)δ 0.72∼1.04(3H,m), 1.04∼3.18(22H,m), 3.62(3H,s), 3.70∼4.12(1H,m) 4.43∼4.63(0.5H,m), 4.98∼5.23(0.5H,m), 5.18∼5.35(1H,m), 6.53(1H,dd,J=16 Hz,J=3 Hz), 6.98(1H,dd,J=16 Hz,J=9 Hz).

PREPARATION EXAMPLE 5

Preparation of 16,16-difluoro-15-keto-6,6a-dehydro-6a-carba-PGI$_1$ methyl ester (16,16-difluoro-15-keto-9(O)-methano-Δ$^{6(9\alpha)}$-PGI$_1$ methyl ester)

5-1 Synthesis of (1S,5S,6S,7R)-3-(4-methoxycarbonylbutyl)-6-[4,4-difluoro--3-oxo-(E)-1-octenyl]-7-tetrahydropyranyloxybicyclo[3.3.0oct-2-ene (8):

(1S,5S,6S,7R)-3-(4-Methoxycarbonylbutyl)-6-hydroxymethyl-7-tetrahydropyranyloxybicyclo[3.3.0]oct-2-ene (3') (0.108 g) was dissolved in DMSO. To the solution, a solution of triethylamine (0.90 ml) and sulfur trioxide/pyridine complex (0.488 g) in DMSO was added, and the mixture was stirred at room temperature for 30 minutes. A usual work-up gave a crude aldehyde. The crude aldehyde was dissolved in THF, and reacted with an anion prepared from dimethyl(2-oxo-3,3-difluoroheptyl)phosphate (0.435 g) and sodium hydride. The mixture was heated for 48 hours under reflux, and then neutralized with acetic acid. A crude product obtained after a usual work-up was purified on column chromatography (hexane/ethyl acetate=7/1) to give (1S,5S,6S,7R)-3-(4-methoxycarbonylbutyl)-6-[4,4-difluoro-3-oxo-(E)-1-octenyl ]-7-tetrahydropyranyloxybicyclo[3.3.0]oct-2-ene (8) as a colorless oily product. Yield: 0.091 g (64%)

$^1$H NMR(CDCl$_3$)δ 0.76∼1.05(3H,m), 1.05∼3.17(27H,m), 3.25∼4.15(3H,m), 3.63(3H,s), 4.35∼4.75(1H,m), 5.09∼5.37(1H,m), 6.56(1H,dd,J=15 Hz,J =6 Hz), 6.86∼7.37(1H,m).

5-2 Synthesis of 16,16-difluoro-15-keto-6,6a-dehydro-6a-carba-PGI$_1$ methyl ester (16,16-difluoro-15-keto-9(O)-methano-Δ$^{6(9\alpha)}$-PGI$_1$ methyl ester) (9):

(1S,5S,6S,7R)-3-(4-Methoxycarbonylbutyl)-6-[4,4-difluoro-3-oxo-(E)-1-octenyl ]-7-tetrahydropyranyloxybicyclo[3.3.0]oct-2-ene (8) (0.091 g) was dissolved in a mixture of acetic acid, water and THF (4 : 2 : 1), and the mixture was stirred at 45° C. for 3 hours. The reaction mixture was concentrated under reduced pressure, and a crude product was purified on column chromatography (hexane/ethyl acetate=2/1) to give 16,16-difluoro-15-keto-6,6a-dehydro-6a-carba-PGI$_1$ methyl ester (16,16-difluoro-15-keto-9(O)-methano-Δ$^{6(9\alpha)}$-PGI$_1$ methyl ester) (9) as a colorless oily product. Yield: 0.060 g (80%)

$^1$H NMR(CDCl$_3$)δ 0.76∼1.05(3H,m), 1.05∼3.21(22H,m), 3.62(3H,s), 3.73∼4.17(1H,m), 5.09∼5.43(1H,m), 6.56(1H,d,J=15 Hz), 7.12(1H,dd,J=15 Hz,J=7.5 Hz).

PREPARATION EXAMPLE 6

Preparation of 16(RS)-fluoro-15-keto-6a-carba-PGI$_2$ (16(RS)-fluoro-15-keto-9(O)-methano-PGI$_2$)

6-1 Synthesis of (1S,5S,6S,7R)-3-[4-methoxycarbonyl-1(EZ)-butenyl]-6-hydroxymethyl-7-tetrahydropyranyloxy-bicyclo[3.3.0]oct-2-ene (3):

In the same manner as in 1-2 of the Example 1 the Compound (3) was prepared.

6-2 Synthesis of (1S,5S,6S,7R)-3-[4-methoxycarbonyl-1(EZ)-butenyl]-6-[4(RS)-fluoro-3-oxo-(E)-1-octenyl]-7-tetrahydropyranyloxy-bicyclo[3.3.0]oct-2-ene (5):

In the same manner as in 1-3 of the Example 1 the above Compound (5) was prepared.

6-3 Synthesis of (1S,5S,6S,7R)-3-[4-methoxycarbonyl-1(EZ)-butenyl]-6-[4 (RS)-fluoro-3(RS)-hydroxy-(E)-1-octenyl]-7-tetrahydropyranyloxybicyclo[3.3.0]oct-2-ene (5''):

(1S,5S,6S,7R)-3-[4-Methoxycarbonyl-1(EZ)-butenyl]-6-[4(RS)-fluoro-3-oxo-(E )-1-octenyl]-7-tetrahydropyranyloxybicyclo[3.3.0]oct-2-ene bicyclo[3.3.0]oct-2-ene (5) (0.088g) was dissolved in methanol. Into the solution, sodium borohydride (0.008 g) was added at 0° C. and the mixture was stirred for 30 minutes. The reaction mixture was treated by a usual manner to give (1S,5S,6S,7R)-3-[4-methoxycarbonyl-1(EZ)-butenyl]-6-[4(RS)-fluoro-3(R S)-hydroxy-(E)-1-octenyl]-7-tetrahydropyranyloxybicyclo[3.3.0]oct-2-ene (5'') as a colorless oily product. Yield: 0.089 g $^1$H NMR(CDCl$_3$)δ0.67~1.03(3H,m), 1.03~3.19(24H,m), 3.22~4.34(4.5H,m), 3.62(3H,s), 4.40~4.74(1.5H,m), 5.07~6.32(5H,m).

6-4 Synthesis of (1S,2S,3R,5S)-(E)-7-(4-methoxycarbonylbutylidene)-2-[4(RS )-fluoro-3(RS)-hydroxy(E)-1-octenyl]-3-tetrahydropyranyloxybicyclo[3.3.0]octane (12'):

(1S,5S,6S,7R)-3-[4-Methoxycarbonyl-1(EZ)-butenyl]-6-[4(RS)-fluoro-3(RS )-hydroxy-(E)-1-octenyl-7-tetrahydropyranyloxybicyclo[3.3.0]oct-2-ene (5'') (0.089 g) was placed in an autoclave and dissolved in acetone. Into the solution, tricarbonyl chromium/methyl benzoate complex (0.011 g) was added, and then the autoclave was degassed. The mixture in the autoclave was stirred under hydrogen pressure of 70 kg/cm$^2$ at 120° C. for 15 hours. The reaction mixture was concentrated under reduced pressure, and the obtained crude product was purified on column chromatography (hexane/ethyl acetate=2/1) to give (1S,2S,3R,5S)-(E)-7-(4-methoxycarbonylbutylidene)-2-[4(RS)-fluoro-3(RS)-hydroxy(E)-1-octenyl]-3-tetrahydropyranyloxybicyclo[3.3.0]octane (12') as a colorless oily product. Yield: 0.078 g (87%)

$^1$H NMR(CDCl$_3$)δ 0.70~1.04(3H,m), 1.04~2.67(28H,m), 3.21~4.32(4.5H,m), 4.36~4.75(1.5H,m), 4.99~5.30(1H,m), 5.30~5.92(2H,m).

6-5 Synthesis of (1S,2S,3R,5S)-(E)-7-(4-Carboxybutylidene)-2-[4(RS)-fluoro-3(RS)-hydroxy-(E)-1-octenyl]-3-tetrahydropyranyloxybicyclo[3.3.0]octane (13'):

(1S,2S,3R,5S)-(E)-7-(4-Methoxycarbonylbutylidene)-2-[4(RS)-fluoro-3(RS)-hydroxy(E )-1-octenyl]-3-tetrahydropyranyloxybicyclo[3.3.0]octane (12') (0.129 g) was dissolved in methanol. Into the solution, 1N aqueous solution of sodium hydroxide (2 ml) was added, and the mixture was stirred at room temperature for 6 hours. After a usual work-up (1S,2S,3R,5S)-(E)-7-(4-carboxybutylidene)-2-[4(RS)-fluoro-3(RS)-hydroxy -hydroxy-(E)-1-octenyl-3-tetrahydropyranyloxybicyclo [3.3.0]octane (13') was obtained as a colorless oily product. Yield: 0.140 g $^1$H NMR(CDCl$_3$)δ 0.70~1.05(3H,m), 1.05~2.70(27H,m), 3.26~6.06(10H,m).

6-6 Synthesis of (1S,2S,3R,5S)-(E)-7-(4-carboxybutylidene)-2-[4(RS)-fluoro -3-oxo-(E)-1-octenyl]-3-tetrahydropyranyloxybicyclo[3.3.0]octane (14'):

(1S,2S,3R,5S)-(E)-7-(4-Carboxybutylidene)-2-[4(RS)fluoro-3(RS)-hydroxy-(E)-1-octenyl]-3-tetrahydropyranyloxybicyclo[3.3.0]octane (13') (0.140 g) was subjected to Jones oxidation between −15° C. and −20° C. The mixture was stirred for 30 minutes, isopropyl alcohol was added to the mixture, and the resultant was treated by a usual work-up. The obtained crude product was purified on column chromatography (hexane/ethyl acetate=6/1−5/1) to give (1S,2S,3R,5S)-(E)-7-(4-carboxybutylidene)-2-[4(RS)-fluoro-3-oxo-(E)-1-octenyl]-3-tetrahydropyranyloxybicyclo[3.3.0]octane (14') as a colorless oily product. Yield: 0.106 g (76%)

$^1$H NMR(CDCl$_3$)δ 0.75~1.04(3H,m), 1.04~2.78(27H,m), 3.23~4.14(3H,m), 4.37~4.73(1.5H,m), 5.02~5.36(1.5H,m), 6.32~6.67(1H,m), 6.73~7.26(1H,m).

6-7 Synthesis of 16(RS)-fluoro-15-keto-6a-carba-PGI$_1$ (16(RS)-fluoro-15-keto-9(O)-methano-PGI$_2$) (15'):

(1S,2S,3R,5S)-(E)-7-(4-Carboxybutylidene)-2-[4(RS)-fluoro -3-oxo-(E)-1-octenyl]-3-tetrahydropyranyloxybicyclo [3.3.0octane (1440) (0.106 g) was dissolved in a mixture of acetic acid, water and THF (4:2:1), and the mixture was stirred at 45° C. for 3.5 hours. The reaction mixture was concentrated under reduced pressure. The crude product was purified on column chromatography (hexane/ethyl acetate=6/1−2/1) using silica gel (CC-4: available from Mallineckrodt Co., Ltd.) to give 16(RS)-fluoro-15-keto-6a-carba-PGI$_2$ (16(RS)-fluoro-15-keto-9(O)-methano-PGI$_2$) (15') as a colorless oily product. Yield: 0.047 g (52%)

$^1$H NMR(CDCl$_3$)δ 0.74~1.04(3H,m), 1.04~2.80(21H,m), 3.67~4.07(1H,m), 4.43~4.65(0.5H,m), 4.99~5.37(1.5H,m), 4.00~5.60(2H,brs), 6.51(1H,dd,J=17 HZ, J=4 Hz), 6.94(1H,dd,J=17 Hz,J=7 Hz).

PREPARATION EXAMPLE 7

Preparation of 16,16-difluoro-15-keto-6a-carba-PGI$_2$ (16,16-difluoro-15-keto-9(O)-methano-PGI$_2$)

7-1 Synthesis of (1S,5S,6S,7R)-3-[4-methoxycarbonyl-1(EZ)-butenyl]-6-[4 ,4-difluoro-3-oxo-(E)-1-octenyl]-7-tetrahydropyranyloxybicyclo[3.3.0]oct-2-ene (16):

(1S,5S,6R,7R)-3-[4-methoxycarbonyl-1(EZ)-butenyl]6-hydroxymethyl-7-tetrahydropyranyloxybicyclo[3.3.0]oct-2-ene(3) (0.333 g) was subjected to Collins oxidation in methylene chloride at 0° C. After 30 minutes sodium hydrogen sulfate was added into the reaction mixture, and the mixture was filtrated. The filtrate was concentrated under reduced pressure to give crude aldehyde (4), which was dissolved in THF, and reacted at 70° C. with an anion prepared from dimethyl(2-oxo-3,3-difluoroheptyl)phosphonate (0.970 g) and sodium hydride. After stirring for 17 hours, the reaction product was neutralized by acetic acid. A crude product obtained after a usual work-up was purified by column chromatography (hexane/ethyl acetate=6/1) to give (1S,5S,6S,7R)-3-[4-methoxycarbonyl-1(EZ)-butenyl]-6-[4,4-difluoro-3-oxo-(E )-1-octenyl]-7-tetrahydropyranyloxy-bicyclo[3.3.0 oct-2-ene (16) as a colorless oily product. Yield: 0.196 g (43%) $^1$H NMR(CDCl$_3$)δ 0.73~1.06(3H,m), 1.04~2.90(23H,m), 2.90~4.17(3H,m), 3.63(3H,s), 4.33~4.71(1H,m), 5.10~5.66(2H,m), 5.94(0.67H,d,J=12 Hz), 6.22(0.33H,dJ=16.5 Hz), 6.57(1H,dd,J=15 Hz,J=6 Hz), 6.86~7.33(1H,m).

7-2 Synthesis of (1S,5S,6S,7R)-3-[4-methoxycarbonyl-1(EZ)-butenyl]-6-[4,4-difluoro-3(RS)hydroxy-(E)-1-octenyl]-7-tetrahydropyranyloxy-bicyclo[3.3.0]oct-2-ene (17):

(1S,5S,6S,7R)-3-[4-Methoxycarbonyl-1(EZ)-butenyl]-6-[4,4-difluoro-3-oxo-(E)-1-octenyl]-7-tetrahydropyranyloxy-bicyclo[3.3.0]oct-2-ene (16) (0.196 g) was dissolved in methanol. To the solution, sodium borohydride (0.015 g) was added at 0° C., and the mixture was stirred for 30 minutes. After a usual work-up (1S,5S,6S,7R)-3-[4-methoxycarbonyl-1(EZ)-butenyl]-6-[4, 4-difluoro-3-(RS)hydroxy-(E)-1-octenyl]-7-tetrahydropyranyloxy-bicyclo[3.3.0]oct-2-ene (17) was obtained as a colorless oily product. Yield: 0.184 g (93%)

$^1$H NMR(CDCl$_3$)δ 0.70~1.03(3H,m), 1.03~2.72(24H,m), 2.85~3.23(1H,m), 3.23~3.96(2H,m), 3.63(3H,s), 3.96~4.35(1H,m), 4.46~4.68(1H,m), 5.05~6.35(5H,m).

7-3 Synthesis of (1S,2S,3R,5S)-(E)-7-(4-methoxycarbonylbutylidene)-2-[4, 4-difluoro-3(RS)-hydroxy-(E)-1-octenyl]-3-tetrahydropyranyloxybicyclo[3.30]octane (18):

(1S,5S,6S,7R)-3-[4-Methoxycarbonyl-1(EZ)-butenyl]-6-[4,4-difluoro-3(RS) hydroxy-(E)-1-octenyl]-7-tetrahydropyranyloxybicyclo[3.3.0]oct-2ene (17) (0.184 g) was dissolved in acetone and the solution was placed in an autoclave, into which tricarbonyl chromium/methyl benzoate complex (0.021 g) was added, and then the autoclave was degassed. The mixture in the autoclave was stirred under hydrogen pressure (70 kg/cm$^2$) at 120° C. for 15 hours. The reaction mixture was concentrated under reduced pressure, and the obtained crude product was purified on column chromatography (hexane/ethyl acetate=7/2−3/1) to give (1S,2S,3R,5S)-(E)-7-(4-methoxycarbonylbutylidene)-2-[4,4-difluoro-3(RS)-hydroxy-(E)-1-octenyl]-3-tetrahydropyranyloxybicyclo[3.3.0]octane (18) as a colorless oily product. Yield: 0.175 g (95%)

$^1$H NMR(CDCL$_3$)δ 0.75~1.05(3H,m), 1.05~2.63(28H,m), 3.23~4.00(3H,m), 3.62(3H,s), 4.00~4.40(1H,m), 4.48~4.66(1H,m), 5.03~5.32(1H,m), 5.33~6.05(2H,m).

7-4 Synthesis of (1S,2S,3R,5S)-(E)-7-(4-carboxybutylidene)-2-[4,4-difluoro-3(RS)-hydroxy-(E)-1-octenyl]-3-tetrahydropyranyloxybicyclo[3.3.0]octane (19):

(1S,2S,3R,5S)-(E)-7-(4-Methoxycarbonylbutylidene)-2-[4,4-difluoro-3(RS)-hydroxy-(E)-1-octenyl]-3-tetrayhydropyranyloxybicyclo[3.3.0]octane (18) (0.175 g) was dissolved into methanol. To the solution, 1N aqueous solution of sodium hydroxide was added, and the mixture was stirred until it became completely clear. After a usual work-up a crude product, (1S,2S,3R,5S)-(E)-7-(4-carboxybutylidene)-2-[4,4-difluoro-3(R S)-hydroxy-(E)-1-octenyl]-3-tetrahydropyranyloxybicyclo[3.3.0]octane (19), was obtained. Yield: 0.172 g $^1$H NMR (CDCl$_3$)δ 0.70~1.03(3H,m), 1.03~2.73(27H,m), 3.22~4.39(4H,m), 4.40~4.72(1H,m), 4.98~5.35(1H,m), 5.35~6.03(2H,m), 3.22~6.13(2H,brs).

7-5 Synthesis of (1S,2S,3R,5S)-(E)-7-(4-carboxybutylidene)-2-[4,4-difluoro-3-oxo-(E)-1-octenyl]-3-tetrahydropyranyloxybicyclo[3.3.0]octane (20):

(1S,2S,3R,5S)-(E)-7-(4-Carboxybutylidene)-2-[4,4-difluoro-3(RS)-hydroxy-(E)-1-octenyl]-3-tetrahydropyranyloxybicyclo[3.3.0]octane (19) (0.172 g) was subjected to Collins oxidation at room temperature. The mixture was stirred for 30 minutes, sodium hydrogen sulfonate was added to the mixture, and then the mixture was filtered. The filtrate was concentrated. The obtained crude product was purified on column chromatography (hexane/ethyl acetate=20/1−10/1) using a silica gel (CC-4) to give (1S,2S,3R,5S)-(E)-7-(4-carboxybutylidene)-2-[4,4-difluoro-3-oxo-(E)-1-octenyl]-3-tetrahydropyranyloxy-bicyclo[3.3.0]octane (20). Yield: 0.050 g (30)

$^1$H NMR(CDCl$_3$)δ 0.66~1.03(3H,m), 1.03~2.75(27H,m), 3.24~4.08(3H,m), 4.36~4.68(1H,m), 5.07~5.36(1H,m), 6.52(1H,dd,J=15 Hz, J=6 Hz), 7-6 Synthesis of 16,16-difluoro-15-keto-6a-carba-PGI$_2$ (16,16-difluoro-15-keto-9(O)-methano-PGI$_2$) (21):

(1S,2S,3R,5S)-(E)-7-(4-Carboxybutylidene)-2-[4,4-difluoro-3-oxo-(E)-1-octenyl]-3-tetrahydropyranyloxybicyclo[3.3.0]octane (20) (0.050 g) was dissolved in a mixture of acetic acid, water and THF (4:2:1), and the mixture was stirred at 45° C. for 3.5 hours. The reaction mixture was concentrated under reduced pressure, and the obtained crude product was purified on column chromatography (hexane/ethyl acetate=4/1) using a silica gel (CC-4) to give 16,16-difluoro-15-keto-6a-carba-PGI$_2$ (16,16-difluoro-15-keto-9( O)-methano-PGI$_2$) (21) as a colorless oily product. Yield: 0.033 g (80%)

$^1$H NMR(CDCL$_3$)δ 0.70~1.05(3H,m), 1.05~2.90(21H,m), 3.65~4.20(1H,m), 5.05~5.40(1H,m), 4.80~5.95(2H,brs), 6.53(1H,d,J=16 Hz), 7.07(1H,dd,J=16 Hz, J=7.5 Hz

FORMULATION EXAMPLE 1

Powders for injection

|  | (Parts by weight) |
|---|---|
| 6a-carba-PGI$_2$ [9(O)-methano-PGI$_2$] | 1 |
| mannitol | 5 |
| distilled water | 0.4 |

The above ingredients were mixed, stirred, sterilized, filtered and lyophilized to give powders for injection.

FORMULATION EXAMPLE 2

Injectable solution

|  | (Parts by weight) |
|---|---|
| 13,14-dihydro-16,16-difluoro-15-keto-6,6a-dehydro-6a-carba-PGI$_1$ [13,14-dihydro-16,16-difluoro-15-keto-9(O)-methano-Δ$^{6(9α)}$-PGI$_1$] | 0.2 |
| nonion surfactant | 2 |
| distilled water | 98 |

The above ingredients were mixed and sterilized to give and injectable solution.

FORMULATION EXAMPLE 3

Enteric capsules 13,14-dihydro-15-keto-16-R,S-fluoro-6a-carba-PGI$_2$ methyl ester [13,14-dihydro-15-keto-16R,S-fluoro-9(O)- methano-PGI₂ methyl ester] (50 mg) dissolved in methanol (10ml) was mixed with mannitol (18.5 g). The mixture was screened (with a sieve, the pore size of which being 30 mm in diameter), dried at 30° C. for 90 minutes and screened again. The powders thus obtained were mixed with fine-grain silica gel (Aerosil*, 200 g) and filled in No. 3 hard gelatin capsules (100) to give enteric capsules which contain 0.5 mg of 13,14-dihydro-15-keto-16R,S-fluoro-6a-carba-PGI₂ methyl ester [13,14-dihydro-15-keto-16R,S-fluoro-9(O)-methano-PGI₂ methyl ester] per capsule.

* Trade Mark

FORMULATION EXAMPLE 4

Powders for oral administration

|  | (Parts by weight) |
|---|---|
| 15-keto-6a-carba-PGI₂ [16,16-difluoro-15-keto-9(O)-methano-PGI₂] | 5 |
| light anhydrous silicic acid | 5 |
| Abicel* | 20 |
| lactose | 70 |

*Trade Mark

The above ingredients were mixed to give powders for oral administration.

FORMULATION EXAMPLE 5

Soft gelatin capsules

|  | (Parts by weight) |
|---|---|
| 16R,S-fluoro-15-keto-6,6a-dehydro-6a-carba-PGI₁ methyl ester [16R,S-fluoro-15-keto-9(O)-methano-PGI₁ methyl ester] | 1 |
| light anhydrous silicic acid | 899 |
| Panasate* | 20 |

*Trade Mark

The above ingredients were mixed and filled in soft gelatin capsules.

FORMULATION EXAMPLE 6

Ophthalmic solution

| 6,6a-dehydro-6a-carba-PGI₁ [9(O)-methano-Δ⁶⁽⁹ᵃ⁾-PGI₁] | 10 mg |
|---|---|
| Physiological Saline | 10 ml |

The above components were placed in separate vials. The vials were combined for preparing a solution on actual use.

TEST EXAMPLE 1

Wistar rats (3 weeks old, weight: 40 to 50g) were allotted into 3 group, each group consisting of 6 animals. The groups were fed with 30% galactose diet.

The test groups subcutaneously received 4 times doses of test compounds dissolved in 5 ml/kg physiological saline, while the control group received 4 times doses of pure physiological saline.

The eyes of the rats were observed every day and the day on which the nucleus of crystalline lens was distinctly opaque as compared with nuclei of the control group was taken as the day of onset of cataract.

On days 24, onset of cataract was observed for all the animals in the control group. The rate of cataract in percent was calculated for all the test groups on day 24.

The results are shown in the following Table 1.

TABLE 1

| Group (n) | Dose*(μg/kg/day) | Rate of cataract (%) |
|---|---|---|
| Control | — | 100 |
| Test compound 1 | 100 | 75 |
| Test compound 1 | 20 | 83 |
| Test compound 2 | 400 | 92 |
| Test compound 3 | 400 | 75 |

*Total amount of four divided doses a day
Test compound 1: 6a-carba-PGI₂ [9(O)-methano-PGI₂]
Test compound 2: 15-keto-6,6a-dehydro-6a-carba-PGI₁ methyl ester [15-keto-9(O)-methano-Δ⁶⁽⁹ᵃ⁾-PGI₁ methyl ester]
Test compound 3: 11β-15-keto-6,6a-dehydro-6a-carba-PGI₁ methyl ester [11β-15-keto-9(O)-methano-Δ⁶⁽⁹ᵃ⁾-PGI₁ methyl ester]

It can be seen from the above results that the test compounds have an activity inhibiting experimental cataract.

What is claimed is:

1. A method for treatment of cataract which comprises administering to a subject in need of such treatment, a prostacyclin compound of formula (I) in an amount effective in treatment of cataract

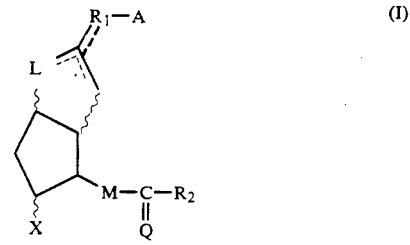

wherein the symbol of a line with a dotted line is a single bond or a double bond provided that only one of the three such symbols can be a double bond, X is hydrogen, hydroxy, halo, lower alkyl, or hydroxy(lower)alkyl, A is —CH₂OH, —COCH₂OH, —COOH or its functional derivative, L is oxygen, carbon, sulfur or nitrogen atom, M is —CH₂—CH₂—, —CH=CH— or —C≡C—, O is oxo,

wherein R₃ is hydrogen or lower alkyl, R₁ is bivalent saturated or unsaturated, lower or medium aliphatic hydrocarbon residue, which is unsubstituted or substituted with halogen, hydroxy, oxo, lower alkoxy, lower alkanoyloxy, cyclo(lower)alkyl, aryl or aryloxy, R₂ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

2. A method according to claim 1, in which said prostacyclin compound is a carbacyclin compound.

3. A method according to claim 1, in which said prostacyclin compound is a prostaglandin I compound.

4. A method according to claim 3, in which said prostaglandin I compound is selected from the group consisting of 6a-carba-PGI₂ [9(O)-methano-PGI₂], 15-keto-6,6a-dehydro-6a-carba-PGI₁ methyl ester [15-keto-9(O)-methano-Δ⁶⁽⁹ᵃ⁾-PGI₁ methyl ester], and 11β-15-keto-6,6a-dehydro-6a-carba-PGI₁ methyl ester [11β-15-keto-9(O)-methano-Δ⁶⁽⁹ᵃ⁾-PGI₁ methyl ester].

* * * * *